(12) United States Patent
Desai

(10) Patent No.: US 10,709,501 B2
(45) Date of Patent: *Jul. 14, 2020

(54) CATHETER AND METHOD FOR IMPROVED ABLATION

(71) Applicant: Sirona Medical Technologies, Inc., Andover, MA (US)

(72) Inventor: Jawahar M. Desai, Roseville, CA (US)

(73) Assignee: Sirona Medical Technologies, Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/262,332

(22) Filed: Jan. 30, 2019

(65) Prior Publication Data
US 2019/0159836 A1    May 30, 2019

Related U.S. Application Data

(60) Continuation of application No. 15/661,606, filed on Jul. 27, 2017, which is a continuation of application
(Continued)

(51) Int. Cl.
*A61B 18/14* (2006.01)
*A61B 18/00* (2006.01)

(52) U.S. Cl.
CPC ............ *A61B 18/1492* (2013.01); *A61B 2018/00029* (2013.01); *A61B 2018/00214* (2013.01);
(Continued)

(58) Field of Classification Search
CPC . A61B 18/14; A61B 18/1492; A61B 18/1402; A61B 2018/1467;
(Continued)

(56) References Cited

U.S. PATENT DOCUMENTS

| 4,940,064 A | 7/1990 | Desai |
| 5,230,349 A | 7/1993 | Langberg |

(Continued)

FOREIGN PATENT DOCUMENTS

| CN | 1674836 A | 9/2005 |
| EP | 1245196 A1 | 10/2002 |

(Continued)

OTHER PUBLICATIONS

Demazumder et al. (2001) "Comparison of Irrigated Electrode Designs for Radiofrequency Ablation of Myocardium," Journal of Interventional Cardiac Electrophysiology. 5:391-400.
(Continued)

*Primary Examiner* — Thomas A Giuliani
(74) *Attorney, Agent, or Firm* — Mintz Levin Cohn Ferris Glovsky and Popeo, P.C.

(57) ABSTRACT

An ablation electrode is mounted on the distal end of a catheter with a first portion inside and a second portion outside the catheter. The second portion is adapted to have a surface that makes maximum contact with a tissue to be ablated, leaving a minimum area not covered by the tissue and potentially exposed to blood. The first portion is adapted to provide an extended surface area for efficient exchange of heat with a coolant flowing inside the catheter. Outlets provided near the area not covered by the tissue in the second portion prevents blood from getting close to or come directly in contact with the area, thereby greatly reducing formation of dangerous blood clots. The minimizing of an electrical circuit through blood greatly reduces wasted power into the electrode so that the efficiently cooled electrode is not burdened. The catheter preferably has multiple electrodes with similar features.

24 Claims, 13 Drawing Sheets

Related U.S. Application Data

No. 14/535,532, filed on Nov. 7, 2014, now Pat. No. 9,717,558, which is a division of application No. 12/173,794, filed on Jul. 15, 2008, now Pat. No. 8,882,761.

(52) U.S. Cl.
CPC ............ *A61B 2018/00351* (2013.01); *A61B 2018/00577* (2013.01); *A61B 2018/00702* (2013.01); *A61B 2018/00791* (2013.01); *A61B 2018/00839* (2013.01); *A61B 2018/00898* (2013.01); *A61B 2018/1475* (2013.01); *A61B 2218/002* (2013.01)

(58) Field of Classification Search
CPC .... A61B 2018/1472; A61B 2018/1475; A61B 2018/1417; A61B 2018/142; A61B 2018/00577; A61B 2018/00589; A61B 2018/00595; A61B 2018/00351; A61B 2018/00357; A61B 2018/00363; A61B 2018/00005; A61B 2018/00011; A61B 2018/00029; A61B 2018/00214; A61B 2218/002
USPC .... 606/41, 40, 49, 32, 34; 607/98–102, 104, 607/105, 113, 115, 116, 119, 122, 129
See application file for complete search history.

(56) References Cited

U.S. PATENT DOCUMENTS

| | | | |
|---|---|---|---|
| 5,342,357 A | | 8/1994 | Nardella |
| 5,383,917 A | * | 1/1995 | Desai ............... A61B 18/12 606/31 |
| 5,688,267 A | | 11/1997 | Panescu et al. |
| 5,843,152 A | * | 12/1998 | Tu ............... A61B 18/1492 607/122 |
| 5,897,553 A | * | 4/1999 | Mulier ............ A61B 18/1402 606/41 |
| 6,053,912 A | | 4/2000 | Panescu et al. |
| 6,217,574 B1 | | 4/2001 | Webster |
| 6,217,576 B1 | * | 4/2001 | Tu ............... A61B 18/1492 606/41 |
| 6,522,905 B2 | | 2/2003 | Desai |
| 6,738,673 B2 | | 5/2004 | Desai |
| 7,151,964 B2 | | 12/2006 | Desai et al. |
| 7,429,261 B2 | | 9/2008 | Kunis et al. |
| 7,632,266 B2 | | 12/2009 | Scopton et al. |
| 7,857,810 B2 | | 12/2010 | Wang et al. |
| 8,882,761 B2 | * | 11/2014 | Desai ............ A61B 18/1492 606/41 |
| 9,717,558 B2 | | 8/2017 | Desai |
| 2002/0062123 A1 | | 5/2002 | McClurken et al. |
| 2005/0070894 A1 | | 3/2005 | McClurken |
| 2005/0090816 A1 | * | 4/2005 | McClurken ........ A61B 18/1206 606/41 |
| 2006/0079873 A1 | * | 4/2006 | Scopton ........ A61B 17/320016 606/37 |
| 2006/0184165 A1 | | 8/2006 | Webster et al. |
| 2007/0083194 A1 | | 4/2007 | Kunis et al. |
| 2008/0045943 A1 | | 2/2008 | Wittkampf et al. |
| 2008/0161792 A1 | | 7/2008 | Wang et al. |
| 2008/0275440 A1 | | 11/2008 | Kratoska et al. |
| 2017/0319274 A1 | | 11/2017 | Desai |
| 2019/0159836 A1 | | 5/2019 | Desai |

FOREIGN PATENT DOCUMENTS

| | | |
|---|---|---|
| EP | 0830091 B1 | 10/2003 |
| JP | H11504539 A | 4/1999 |
| JP | H11506947 A | 6/1999 |
| JP | 2000201949 A | 7/2000 |
| JP | 2002528213 A | 9/2002 |
| JP | 2005502424 A | 1/2005 |
| JP | 1156156 B2 | 9/2008 |
| WO | 9618349 A2 | 6/1996 |
| WO | 03020339 A2 | 3/2003 |
| WO | 03024349 A1 | 3/2003 |
| WO | 2010/008975 A2 | 1/2010 |

OTHER PUBLICATIONS

Nakagawa et al. (1998) "Inverse Relationship between Electrode Size and Lesion Size During Radiof-requency Ablation with Active Electrode Cooling," Circulation. 98:458-465.

Wittkampf et al. (Nov. 2006) "RF Catheter Ablation: Lessons on Lesions," PACE. 29:1285-1297.

International Search Report with Written Opinion corresponding to International Patent Application No. PCT/US2009/049877, dated Mar. 23, 2010, 18 pages.

Office Action corresponding to Chinese Patent Application No. 200980128036.5, dated Mar. 16, 2012, 12 pages.

Office Action corresponding to Chinese Patent Application No. 200980128036.5, dated Nov. 14, 2012, 1 page.

Office Action corresponding to Chinese Patent Application No. 201310403922.2, dated Aug. 14, 2015, 2 pages.

Office Action corresponding to European Patent Application No. 09790135.9, dated Sep. 22, 2014, 5 pages.

Office Action corresponding to Japanese Patent Application No. 2011-518794, dated Oct. 4, 2013, 6 pages.

Office Action corresponding to Japanese Patent Application No. 2011-518794, dated Jul. 29, 2014, 4 pages.

* cited by examiner

|   |   | Standard Electrode | Improved Irrigated Electrode |
|---|---|---|---|
| (A) | Electrode Size | Length: 3.5-4.0 mm<br>Diameter: 2.3 mm | Length: 1.5-2.0mm (outside portion)<br>Diameter: 2.3mm |
| (B) | Site of Ablation | 25% Contact with Tissue<br>75% Contact with Blood | 75% Contact with Tissue<br>25% Contact with Blood buffered by Saline 'Cloud' |
| (C) | Electrode Cooling | 37°C Blood Assisted by 20°C Saline | 20°C Saline over an Extended Surface of Electrode |
| (D) | Electrode Ablation Temperature | 35-50 °C | 40-48 °C |
| (E) | Lesion size | Dia: 6mm<br>Depth: 6mm | Dia: 6mm<br>Depth: 6mm |
| (F) | RF Power Input | 35-50 W | 10-15 W |
| (G) | Ablation duration per site | 30-60 s | 15-30 s |
| (H) | Rate of irrigation per Ablation | 30 ml/min | 1-2 ml/min |
| (I) | Potential Risk of Steam Pop | MODERATE (due to less efficient tissue heating and electrode cooling) | LOW due to efficient electrode cooling and efficient heating |
| (J) | Potential Risk of Blood Clot Formation | HIGH due to maximum electrode contact with blood | LOW due to minimum electrode contact with blood |

FIG. 9

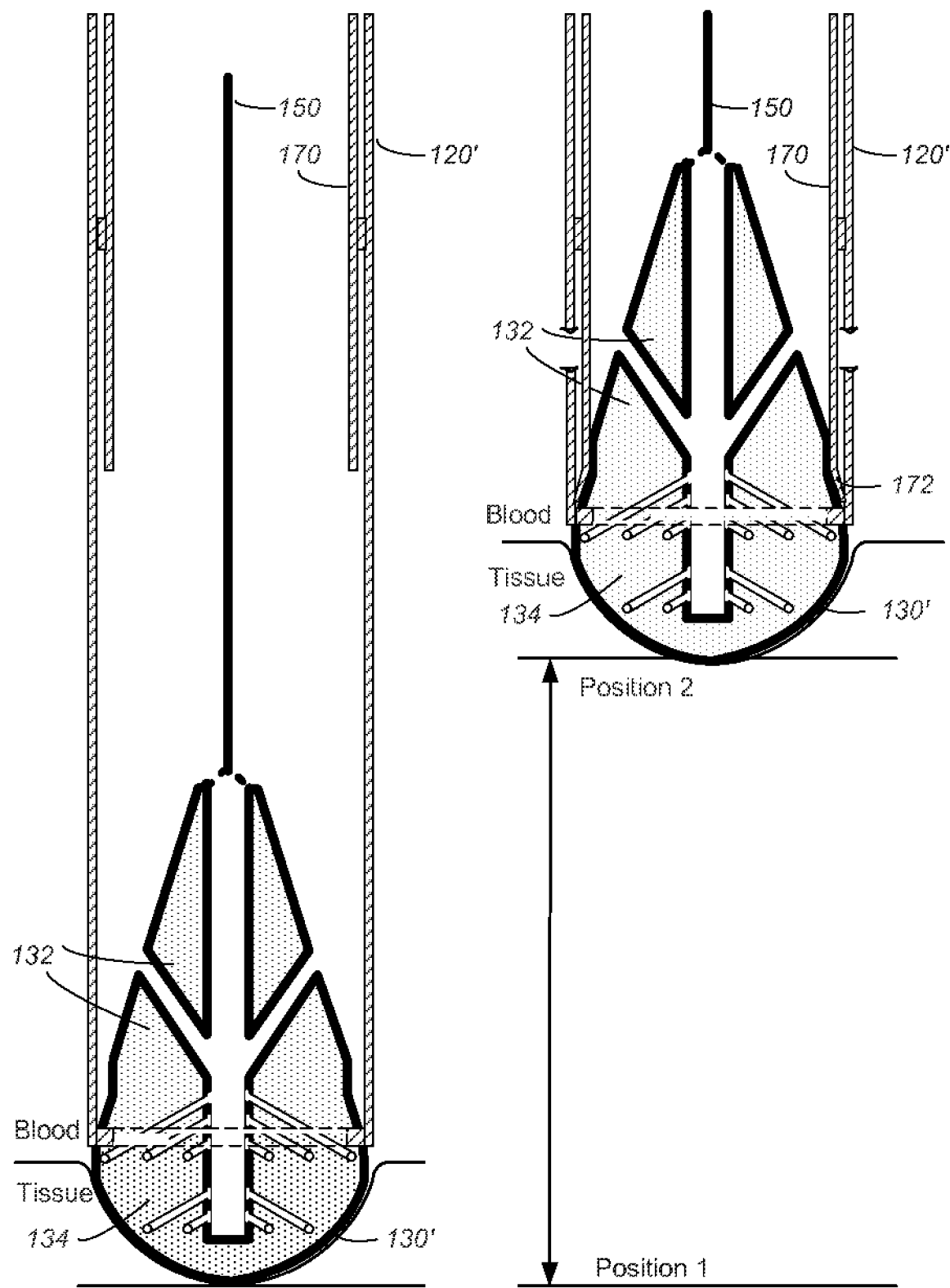
FIG. 12A     FIG. 12B

|   | | Standard Electrode | Improved Irrigated Electrode | Improved 5-electrode Irrigated Catheter |
|---|---|---|---|---|
| (A) | RF Power Input | 35-50 W | 10-15 W | Central Electrode: 10-15 W Peripheral Electrode: 4-5 W |
| (B) | Ablation duration per site | 30-60 s | 15-30 s | 15-30 s |
| (C) | Total number of Ablations for procedure | 40-60 | 40-60 | 8-12 |
| (D) | Total Ablation time for mapping & ablation procedure | 2 hours | 1.5 hours | < 1 hour |
| (E) | Total injection of irrigant for procedure | 3000 ml | 200 ml | 200ml |
| (F) | How Lesion Formation Monitored | Attenuation of Intracardiac electrogram | Attenuation of intracardiac electrogram | Attenuation of Intracardiac electrogram |
| (G) | Potential Risk of Steam Pop | MODERATE (due to less efficient tissue heating and electrode cooling) | LOW due to efficient electrode cooling and efficient heating | LOW due to efficient electrode cooling and efficient heating |
| (H) | Potential Risk of Blood Clot | HIGH due to maximum electrode contact with blood | LOW due to minimum electrode contact with blood | LOW due to minimum electrode contact with blood |

FIG. 14

CATHETER AND METHOD FOR IMPROVED ABLATION

CROSS-REFERENCE TO RELATED APPLICATIONS

The present application is a continuation of U.S. patent application Ser. No. 15/661,606 entitled "Catheter and Method for Improved Ablation," filed Jul. 27, 2017, which is a continuation of U.S. patent application Ser. No. 14/535,532 (now U.S. Pat. No. 9,717,558) entitled "Catheter and Method for Improved Ablation," filed Nov. 7, 2014, which is a divisional of U.S. patent application Ser. No. 12/173,794 (now U.S. Pat. No. 8,882,761) entitled "Catheter and Method for Improved Ablation," filed on Jul. 15, 2008, which are hereby incorporated by reference in their entireties.

BACKGROUND

Cardiac dysrhythmias are commonly known as irregular heart beats or racing heart. Two such heart rhythm irregularities are the Wolff-Parkinson-White syndrome and atrioventricular ("AV") nodal reentrant tachycardia. These conditions are caused by an extraneous strand of muscle fiber in the heart that provides an abnormal short-circuit pathway for electric impulses normally existing in the heart. For example, in one type of the Wolff-Parkinson-White syndrome the accessory pathway causes the electric impulses that normally travel from the upper to the lower chamber of the heart to be fed back to the upper chamber. Another common type of cardiac dysrhythmias is ventricular tachycardia ("VT"), which is a complication of a heart attack or reduction of blood supply to an area of heart muscle, and is a life threatening arrhythmia. An even more common type of cardiac dysrhythmias is Atrial Fibrillation which afflicts millions of people worldwide.

In the treatment of cardiac dysrhythmias, non-surgical procedures such as management with drugs are favored. However, some dysrhythmias of the heart are not treatable with drugs. These patients are then treated with either surgical resection of VT site of origin or by Automatic implantable cardiovertor defibrillator ("AICD"). Both procedures have increased morbidity and mortality and are extremely expensive. Even AICD needs major surgical intervention. In addition, some patients of advanced age or illness cannot tolerate invasive surgery to excise tachycardia focus which causes dysrhythmias.

Techniques have been developed to locate regions of tachycardia and to disable their short-circuit function. Radio-frequency energy is applied to ablate the cardiac tissues in those regions so as to produce scars and interrupt conduction.

The regions to be ablated are usually determined by endocardiac mapping. It is a technique that typically involves percutaneously introducing a mapping electrode catheter into the patient. The mapping electrode catheter is passed through a blood vessel, like femoral vein or aorta and thence into an endocardiac site such as the atrium or ventricle of the heart. A tachycardia is induced and a continuous, simultaneous recording made with a multichannel recorder while the electrode catheter is moved to different endocardiac positions. When a tachycardial focus is located as indicated in an electrocardiogram recording, it is marked by means of a fluoroscope image.

Upon locating of the tachycardial focus, ablation of cardiac arrhythmias is typically performed by a standard ablating electrode catheter placed at the focus. The Radio-frequency energy is used to create a lesion in the endocardiac tissues adjacent (i.e. underneath) the standard electrode catheter. By creating one or more lesions, the tachycardial focus may be turned into a region of necrotic tissue, thereby disabling any malfunctions.

Conventional catheter ablation techniques have typically employed a catheter with a single electrode at its tip as one electrical pole. The other electrical pole is formed by a backplate in contact with a patient's external body part. These techniques have been used successfully for interruption or modification of conduction across the atrioventricular (AV) junction in AV nodal reentrant tachycardia; for interruption of accessory pathway in patients with reentrant tachycardia due to Wolff-Parkinson-White Syndrome; and for ablation in some patients with ventricular tachycardia.

In one technique, high voltage direct current ("DC") in the range of 100 to 300 joules is applied across the electrode and the backplate to effect ablation. Direct current energy source using the standard electrode catheter can produce a lesion size larger than the footprint of the electrode. However, the lesion dimensions are variable at the same energy output and they do not have clear demarcation from the surrounding tissues. Additionally, high voltage techniques have other undesirable side-effects such as barotrauma and the lesions formed could become proarrhythmic. This technique is now abandoned.

Another technique is to apply a radio-frequency ("RF") source to a standard electrode catheter. The RF source is typically in the 600 kHz region and produces a sinusoidal voltage between two wires. When this is delivered between the distal tip of a standard electrode catheter and a backplate, it produces a localized RF heating effect. It causes a well defined, discrete lesion slightly larger than the tip electrode. This simple RF ablation technique creates lesion size sufficient for interruption of AV junction or accessory pathway.

RF ablation is preferable to DC ablation because it does not need anesthesia and produces more circumscribed and discrete lesions and avoids injury caused by high voltages as in DC shock.

Generally, catheter ablations of AV junction using standard electrode catheter with DC or RF energy for treating drug resistant supraventricular tachycardia have high success rate with very low incidence of complications. For Cardiac arrhythmias like Superaventricular tachycardia ("SVT"), Idiopathic ventricular tachycardia, Ischemic ventricular tachycardia and more recently Atrial fibrillation Radiofrequency catheter ablation has become principal form of therapy. In 50% of VT and 10% of SVT deeper lesions may be needed and standard 7f 4 mm catheter electrode may be unable to create deeper lesion to ablate arrhythmogenic substrate.

However, in ventricular tachycardia (VT), endocardiac mapping with a standard electrode catheter can locate the exit site of ventricular tachycardia to within 4 to 8 $cm^2$ of the earliest site recorded by the catheter. A standard electrode catheter typically has a maximum electrode tip area of about 0.3 $cm^2$. Therefore, the lesion created by the simple RF technique delivered through a standard electrode catheter may not be large enough to ablate the ventricular tachycardia. Attempts to increase the size of lesion by regulation of power and duration by increasing the size of electrode or by regulating the temperature of tip electrode have met with partial success.

In order to increase the size of the lesion, an orthogonal electrode catheter array (OECA) with four peripheral electrodes and one central electrode has been proposed. Such an OECA has been disclosed by Dr. Jawahar Desai in U.S. Pat. No. 4,940,064, issued Jul. 10, 1990, for use in both mapping and ablation of endocardiac sites.

In spite of the improvements, the need remains for further improvements in creating lesions of desirable size in a minimum of time with minimum undesirable side effects.

It is generally recognized that lesions of larger and deeper size are achieved by increasing the input RF power. One problem has to do with overheating which can cause the ablation system to malfunction and other dangerous side effects, such as the formation of blood clot in the course of RF ablation. Experimental data suggest a lesion is created when myocardial tissue is irreversibly damaged at temperature higher than 50.degree. C. Deeper lesions are produced as catheter tip-tissue interface temperature increases, until the interface temperature reaches 100.degree. C., at which point plasma boils, resulting in coagulum formation at the electrode surface. This can result in clot embolization, a sudden increase in impedance of the ablation circuit, resulting in ineffective tissue heating. More seriously, the blood clots may block blood vessels such as those in the brain and result in the patient suffering a stroke.

Placement of thermocouples and thermistors at the catheter tip allows monitoring of catheter tip temperature, in an attempt to avoid excessive heating. Subsequent RF generators have allowed titration of delivered power until a chosen catheter tip temperature is reached. RF delivery in this mode is referred to as temperature-guided RF ablation. However, this technique necessarily results in a longer ablation time and causes complications that accompany a prolonged procedure.

In order to supply more power without excessive heating, the ablation electrode is cooled to keep the temperature under control. Since blood is at a temperature of about 37 degree centigrade, the electrode is designed to have a large surface area in contact with blood which serves to cool the electrode. The cooling by blood is effective especially in the heart chamber where substantially volume of it is constantly being exchanged.

In situations with low blood flow, the electrode is additionally cooled by irrigation with a coolant. As pointed out in Wittkampf et al, "RF Catheter Ablation: Lessons on Lesions", PACE, Vol. 29, November 2006, pp. 1285-1297, low blood flow may occur in atrial fibrillation or poor left ventricular function. This will result in limited cooling of the electrode and impose a limitation on the amount of power that can safely be applied. Extraneously supplied coolant is used to augment the cooling of the electrode.

The above mentioned techniques help to alleviate some of the problems but also create other undesirable effects such as inefficient power usage, generating a substantial amount of heat from wasted power, long ablation time, excessive amount of coolant introduced into the patient, and still do not eliminate the danger of blood clot formation.

Thus, it is desirable to have catheter ablations that produce lesions of desirable size while performing them more efficiently in less time with less power and coolant and less danger of blood clot formation.

SUMMARY

According to a general aspect of the invention, an improved ablation catheter is provided with an improved electrode that provides maximum contact with the tissue and a minimum exposure to blood. The electrode is disposed at a distal end of the catheter and having a first portion enclosed within the catheter and a second portion exposed to outside of the catheter. The first portion is of a shape having a surface area substantially larger than that of said second portion for exchanging heat with a coolant in the catheter. The second portion is of a shape having a protruding surface that when disposed to ablate a biological tissue is substantially covered by and in contact with the biological tissue while leaving a minimum surface area not in contact with and uncovered by the biological tissue. In spite of the configuration of the second portion, the electrode is adequately cooled by the configuration of the first portion. At the same time, coolant is used to flush the minimally exposed portion of the electrode not covered by the tissue so as to keep the blood away from possible local hot spots around the minimally exposed portion.

In this way a circuit path through the blood is minimized, resulting in less wasted heat generated and the power is efficiently used to heat up the tissue. Since less wasted power is dumped through the electrode, there is less demand on cooling the electrode. More importantly, the electrode is still adequately cooled at the first portion in spite of the diminished exposed second portion of the electrode. Furthermore the coolant is discharged at the exposed second portion in such a manner to discourage blood clot formation. The various features allow the ablation time to be shortened by at least two folds and the amount of coolant discharged to be reduced by ten folds and the danger of blood clot formation to be minimized.

According to another aspect of the invention, the improved electrode is preferably incorporated in a catheter that can have wings fanned out to form a plane with the electrode at the center. In this way, when the catheter is disposed against a tissue, the plane will be hugging the tissue surface and the electrode will impinge on the tissue in a perpendicular direction.

According to yet another aspect of the invention, when an even larger lesion is desired or multiple lesion to be performed in parallel in a procedure, the present inventive features are implemented in an improved multi-electrode catheter which spans a larger ablation zone. Each of the multiple electrodes will incorporate the inventive features.

When employing the improved multi-electrode catheter in a procedure with multiple ablations, the time for performing the procedure is significantly reduced due to several factors. First, the time for each ablation is already halved compared to conventional catheters. Secondly, the number of ablation operation is reduced due to the multiple electrodes performing the ablations in parallel. Thirdly, the same catheter is expediently used for both mapping and ablation. The mapping operation is interleaved with the ablation operation and is used for locating the sites for ablation and for monitoring the quality of the lesion.

According to another aspect of the invention, a method of ablating a biological tissue surrounded by blood, includes providing an electrode having a first portion enclosed within a catheter and a second portion exposed outside the catheter, the first portion being of a shape having a surface area substantially larger than that of the second portion and being in fluid communication with a coolant for exchanging heat therewith, the second portion being of a shape having a protruding surface that when disposed to ablate a biological tissue is substantially covered by and in contact with the biological tissue while leaving a minimum surface area not in contact with and uncovered by the biological tissue, disposing the second portion of the electrode against the biological tissue, and supplying a predetermined amount of RF energy to the electrode to create a lesion of a predetermined size.

Additional objects, features and advantages of the present invention will be understood from the following description of the preferred embodiments, which description should be taken in conjunction with the accompanying drawings.

BRIEF DESCRIPTION OF THE DRAWINGS

FIG. 9 is a table comparing the ablation operating characteristics of a conventional irrigated catheter with that of the preferred embodiment.

FIG. 12A illustrates the relation between the coolant fluid tube and the tip electrode when the peripheral electrodes are not in a deployed configuration.

FIG. 12B illustrates the relation between the coolant fluid tube and the tip electrode when the peripheral electrodes are in a deployed configuration as shown in FIG. 10C.

FIG. 14 is a table comparing projected ablation operating characteristics of different catheters for an ablation procedure to treat atrial fibrillation.

DETAILED DESCRIPTION

Figure 1:
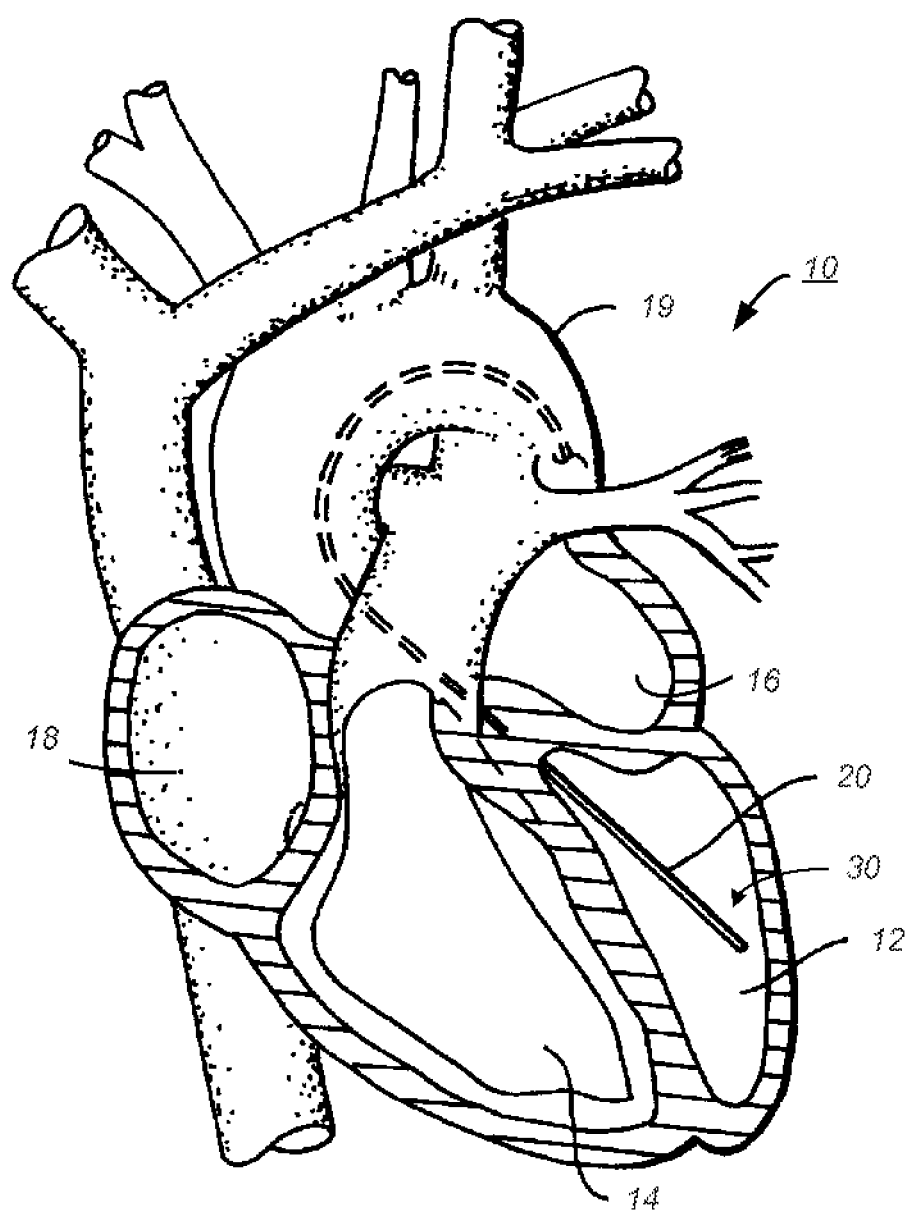
FIG. 1 illustrates schematically a typical application of catheter ablation to pathological tissues inside a heart chamber.

FIG. 1 illustrates schematically a typical application of catheter ablation to pathological tissues inside a heart chamber. Particularly, FIG. 1 shows a front elevational view of a human heart 10 in partial cross-section. In an example of operation, a catheter 20 is percutaneously introduced into a patient and directed through a blood vessel (not shown) and into the aorta 19, as best seen in FIG. 1. The catheter has a distal end 30 positioned within, for example, the left ventricle 12, although it could as easily be placed within the right ventricle 14 or any other endocardial chamber such as the left atrium 16 or the right atrium 18 or another site.

The catheter 20 has one or more electrodes. It first operates in a mapping mode in which electrical signals in the endocardium are detected by the electrodes. As disclosed in U.S. Pat. No. 6,522,905, the entire disclosure of which is incorporated herein by reference, the mapping operation allows the catheter to locate the problem site of origin of tachycardia in the endocardium. Once the problem site is located, the catheter is switched to operate in an ablation mode, when its electrodes often operate in combination with an external body contact electrode. Radiofrequency power is delivered to the combination of electrodes to ablate the problem site.

Ventricular tachycardia ("VT") is a class of arrhythmias due to problems arising from the ventricle. The conditions include Right Ventricular Outflow Tract Trachycardia and Ischemic Ventricular Tachycardia. Similarly, superaventricular tachycardia ("SVT") is another class of arrhythmias due to problems arising above the ventricles such as in the atrium. The conditions include Atrial Tachycardia, AV Nodal Reentry, Wolff Parkinson White Syndrome and Atrial Flutter. Both VT and SVT can be cured by ablating the located problem site or focal point. Atrial Fibrillation is yet another class of arrhythmia. Atrial Fibrillation can be treated by ablating an identified focal site or by ablating lesion lines in the atrium. Many of these conditions can be treated expediently with catheter ablation, without the use of invasive surgery and allow the whole treatment to be completed in a day procedure.

Radiofrequency Energy source has become the preferred modality for catheter ablation of cardiac arrhythmias. RF generators deliver an unmodulated sine wave AC current at a frequency of 500-1000 kHz. In conventional single phase ablation, the current applied is unipolar from the electrode tip of the catheter to a large dispersive patch on the patient's skin. AC current travels from the tip through the tissues to the dispersive patch causes resistive heating. The degree of heating is proportional to the square of the current density. As the ablation catheter tip is small relative to the dispersive patch (typically >10 cm$^2$), this is the site of highest current density and heating. Current density falls with the square of the distance from the electrode; resistive heating therefore falls in proportion to the fourth power with distance. This means that only a small rim (1-1.5 mm) of direct resistive heating is produced around the tip.

It has been determined that raising the temperature of the tissue to about 50 degree Celsius is sufficient to create a lesion. However deeper ablation of tissue is dependent on conductive heating resulted from the 'virtual electrode' of resistive heating. Steep thermal gradients are produced around the electrode tip, with the highest temperature at the tip-tissue interface. In general, tip-tissue interface rises with delivered power and lesion size is proportional to delivered power.

While a deeper and larger size lesion can only be achieved by raising the power, in practice, the amount of delivered power is limited by the consideration of avoiding excessive heating. Excessive heating can result in the production of steam within the tissue, ultimately leading to a "steam pop"

and potentially to crater formation in the adjacent tissue, which can result in significant collateral damage and even cardiac perforation.

Even in less excessive heating cases, as mentioned earlier, there is the danger of thrombus or blood clot formation. Blood clot formation around the electrode can lead to sudden increase in the impedance of the ablation circuit and a sharp drop in power delivered. More insidiously, a certain amount of blood will begin to clot before the rise in impedance would indicate so.

As previously mentioned, boiling of plasma at the electrode tip-tissue interface limits power delivery with standard RF. Two approaches have been devised to increase electrode cooling and thus allow maintenance of effective levels of RF power. The first approach is to increase the electrode surface area exposed to the blood. Since the heart chamber is really a pump for blood at a rate of about 80 ml per sec, the blood pool in which the catheter operates serves to cool the electrode towards the blood temperature at 37 degree Celsius. Thus, conventional catheters are developed with a tip electrode having an axial length of 4 to 8 mm. This greater surface area increases convective cooling. The second approach to this problem, especially in the situation where the blood flow is diminished, is to augment the cooling of the electrode with an extraneously introduced coolant, such as an infusion of saline. Saline infusion allows greater power delivery to the tissue and shifts the point of maximal heating to the tissue itself Ultimately, this results in deeper conductive heating and the production of deeper lesions.

Two types of irrigated catheters have been employed. The first type is the closed-loop irrigation catheter, which continuously circulates saline within the electrode tip, internally cooling the electrode tip. The second type is the open irrigation catheter, which has the coolant flow out of the catheter through multiple irrigation holes located on the electrode or though a sheath near the electrode. Examples of these two types of irrigated catheters have been disclosed in Demazumder et al, "Comparison of Irrigated Electrode Designs for Radiofrequency Ablation of Myocardium", Journal of Interventional Cardiac Electrophysiology 5, 391-400, 2001.

Figure 2A:
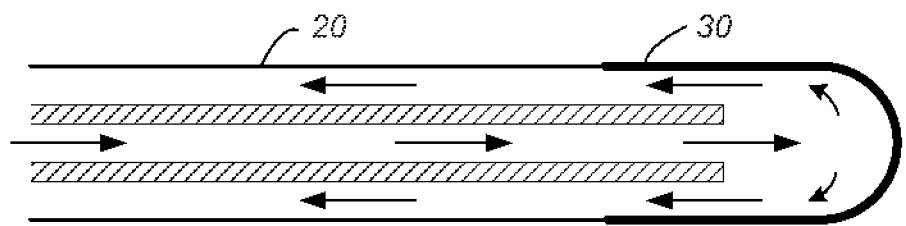
FIG. 2A illustrates a conventional irrigated catheter of the closed-loop design.

FIG. 2A illustrates a conventional irrigated catheter of the closed-loop design. A tip electrode is at the distal end of the catheter. One example of the tip electrode is a metallic shell with a diameter of 2.3 mm and a length of 5 mm. A lumen carries a coolant inside the catheter from an external source (not shown) to the distal end to cool the internal surface of the electrode. The coolant is circulated by returning to the external source though a return path provided by a concentric space between the inner wall of the catheter and the outer wall of the lumen.

Figure 2B:
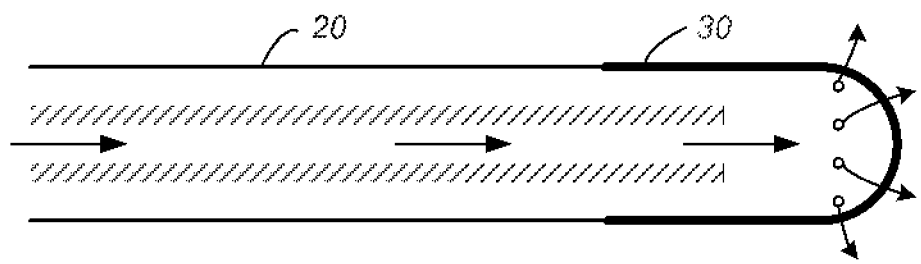
FIG. 2B illustrates a conventional irrigated catheter of the open design in which the coolant exits the catheter through holes located on the electrode.

FIG. 2B illustrates a conventional irrigated catheter of the open design in which the coolant exits the catheter through holes located on the electrode. The tip electrode is similar to that shown in FIG. 2A, except a number of outlets is provided on the electrode for the coolant to exit the catheter. There is no return path inside the catheter for the coolant to return to the source.

Figure 2C:
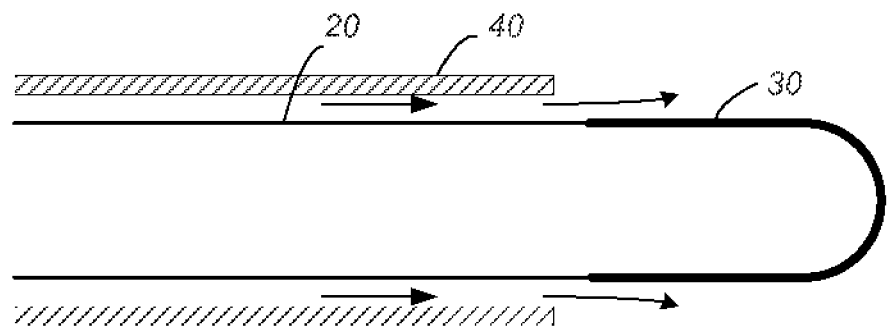
FIG. 2C illustrates a conventional irrigated catheter of the open design in which the coolant exits the catheter through a sheath near the electrode.

FIG. 2C illustrates a conventional irrigated catheter of the open design in which the coolant exits the catheter through a sheath near the electrode. The tip electrode is similar to that shown in FIG. 2A. An outer sheath 40 of the catheter provides a concentric space in between for coolant to be supplied from the external source to the distal end of the catheter. The sheath terminates at the distal end of the catheter just before the electrode with an opening that allows coolant to exit and wash over the electrode.

Figure 3A:
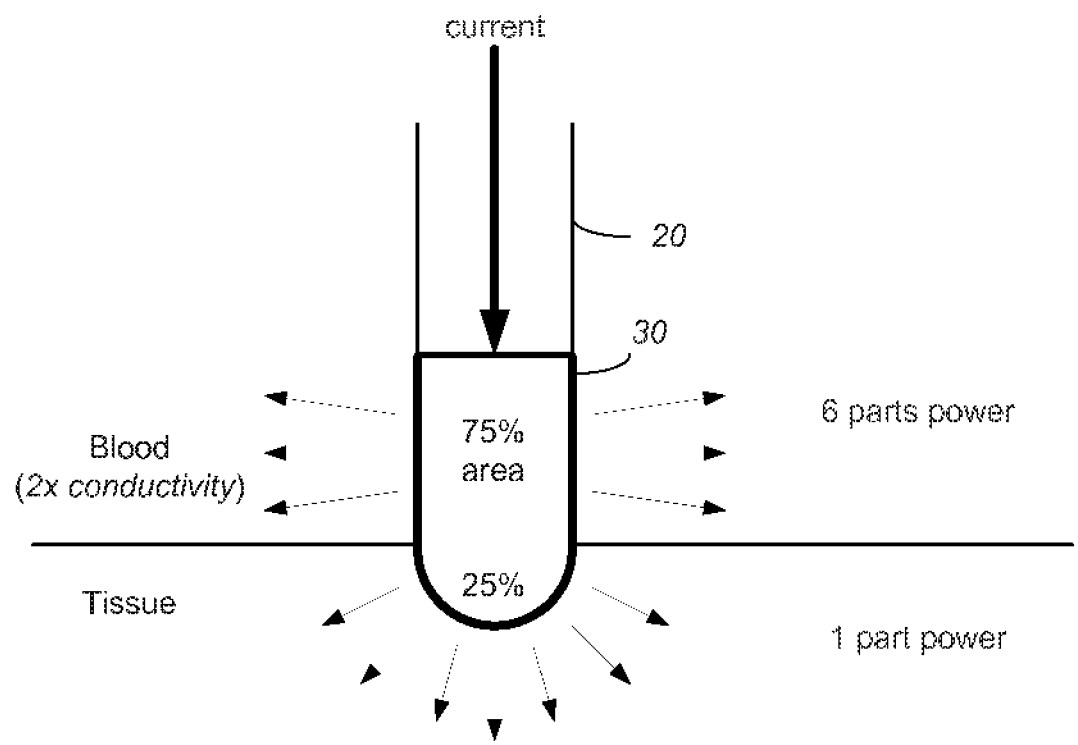
FIG. 3A illustrates the conduction paths around a conventional electrode.

FIG. 3A illustrates the conduction paths around a conventional electrode. Typically for the conventional catheters shown in FIG. 2A-2C, only at most 25% of the surface area of the tip electrode is making contact with the tissue being ablated. The other 75% is exposed to blood for cooling. Since blood turns out to be twice as conductive as the tissue, a substantial portion of the current flows from the electrode to a grounding plate (not shown) via conduction path of the blood rather than via the tissue.

Figure 3B:
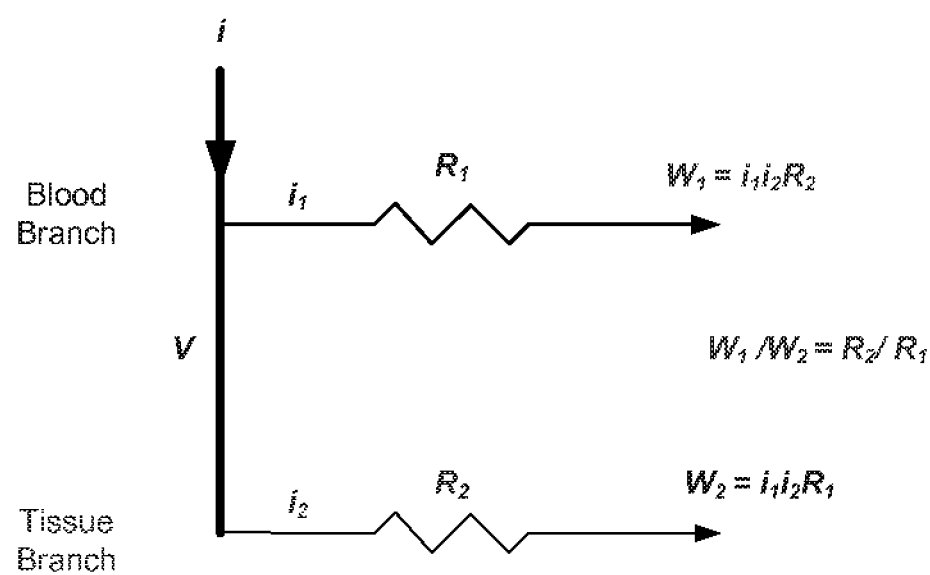
FIG. 3B illustrates schematically an equivalent circuit of the conduction paths of the conventional electrode shown in FIG. 3A.

FIG. 3B illustrates schematically an equivalent circuit of the conduction paths of the conventional electrode shown in FIG. 3A. The equivalent circuit has two branches, one for the pathway from the electrode to the blood and the other for the pathway from the electrode to the tissue. When the electrode is at a potential V, then the blood branch yields $V=i_1R_1$ where $i_1$ is the current flowing in the blood branch and $R_1$ is the impedance. Similarly, the tissue branch yields $V=i_2R_2$. Now the power dissipated in the blood branch is given by $W_2=i_2{}^2R_1=i_1i_2R_2$. Similarly the power dissipated in the tissue branch is given by $W_2/i_2{}^2R_2=i_1\ i_2R_1$. Therefore the ratio of power dissipated in the two branches is $W_2/W_1=R_1/R_2$. In other words, the power in each branch is inversely proportional to the impedance in each branch. For the case of the electrode's exposure to tissue and blood being at a ratio of 1/3 and the blood being twice as conductive as the tissue, $W_2/W_1 \sim 1/6$.

Wittkampf et al, "RF Catheter Ablation: Lessons on Lesions", PACE, Vol. 29, November 2006, pp. 1285-1297 estimates that of all the power supplied to the electrode, about 40% of the power is lost in the rest of the patient, including the area near the ground electrode patch. Of the remaining 60%, only one-seventh of it is delivered to heat the tissue. This means out of a total power of 50 W, only about 9% or about 4.5 W is used to heat up the tissue.

Nakagawa et al, "Inverse Relationship Between Electrode Size and Lesion Size During Radiofrequency Ablation With Active Electrode Cooling", Circulation, 1998; 98; 458-465, essentially comes to the same finding by comparing the ablation characteristics of a 5 mm with a 2 mm long electrode. However, while the shorter electrode is found to be more energy efficient, there is more occurrence of overheating as indicated by steam pops. It appears, in spite of employing irrigation to augment cooling by blood, the shorter electrode provides little surface area for effective heat exchange and the electrode is susceptible to overheating.

In any case, after allowing for the lost to the rest of the patient, for every seven units of power delivered to the electrode, six units go to heat up the blood through the electrode and only one unit is actually directed through the electrode to heat up the tissue. The cooling by blood notwithstanding, this unfavorable power ratio is very inefficient for conventional 4-8 mm long electrodes. Conventional wisdom is to augment the cooling of the electrodes by blood with irrigation. However, apart from being liable to heat up the electrode excessively in an attempt to deliver more power to the tissue, it is also liable to induce blood clot formation.

Figure 4:
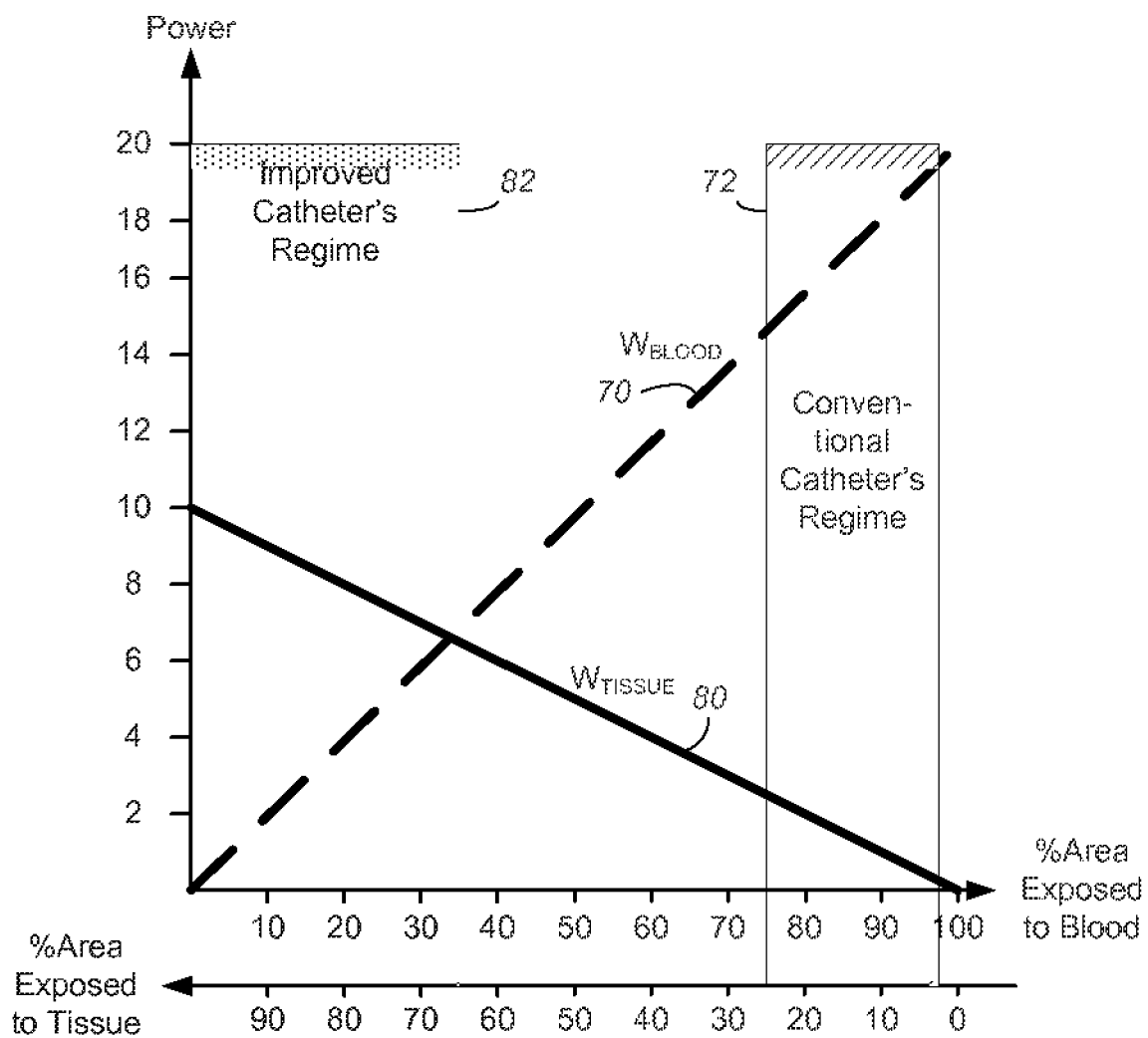
FIG. 4 is a graph illustrating the power regimes of the conventional ablation catheter and the improved catheter of the present invention.

FIG. 4 is a graph illustrating the power regimes of the conventional ablation catheter and the improved catheter of the present invention. The curve 70 (broken line) represents the power dissipated in the blood branch (see FIG. 3B) and the curve 80 (solid line) represents the power dissipated in the tissue branch, as a function of the surface area of the ablating electrode exposed to blood. Two x-axes are shown for convenience. The first represents increasing area of the electrode exposed to blood. The second represents the complement of the first with decreasing area of the electrode covered by the tissue. In view of the discussion earlier, a conventional catheter typically operates in the regime 72, where power supplied to the ablating electrode is disproportionally biased towards the blood branch. In contrast, as the following description will explain, the improved electrode of the present invention is designed to operate in the regime 82 where the power supplied to the tissue branch is maximized and the power dissipated in the blood branch is minimized.

According to a general aspect of the invention, an improved ablation catheter is provided with an improved electrode that provides maximum contact with the tissue and a minimum exposure to blood. The electrode is disposed at a distal end of the catheter and having a first portion enclosed within the catheter and a second portion exposed to outside of the catheter. The first portion is of a shape having a surface area substantially larger than that of said second portion for exchanging heat with a coolant in the catheter. The second portion is of a shape having a protruding surface that when disposed to ablate a biological tissue is substantially covered by and in contact with the biological tissue while leaving a minimum surface area not in contact with and uncovered by the biological tissue. In spite of the configuration of the second portion, the electrode is adequately cooled by the configuration of the first portion. At the same time, coolant is used to flush the minimally exposed portion of the electrode not covered by the tissue so as to keep the blood away from possible local hot spots around the minimally exposed portion.

In this way a circuit path through the blood is minimized, resulting in less wasted heat generated and the power is efficiently used to heat up the tissue. Since less wasted power is dumped through the electrode, there is less demand on cooling the electrode. More importantly, the electrode is still adequately cooled at the first portion in spite of the diminished exposed second portion of the electrode. Furthermore the coolant is discharged at the exposed second portion in such a manner to discourage blood clot formation. The various features allow the ablation time to be shortened by at least two folds and the amount of coolant discharged to be reduced by ten folds and the danger of blood clot formation to be minimized.

In a preferred embodiment, the electrode has a length of 2 mm or less so that a substantial portion if not all of it is buried into and covered by the tissue during ablation. In operation, the electrode is placed perpendicular to the tissue to achieve maximum coverage by the tissue. For any exposed portion of the electrode not covered by the tissue, its contact with blood is buffered by coolant discharging in the vicinity. In this way, the blood is kept away from any hot spots near the electrode.

Figure 5:
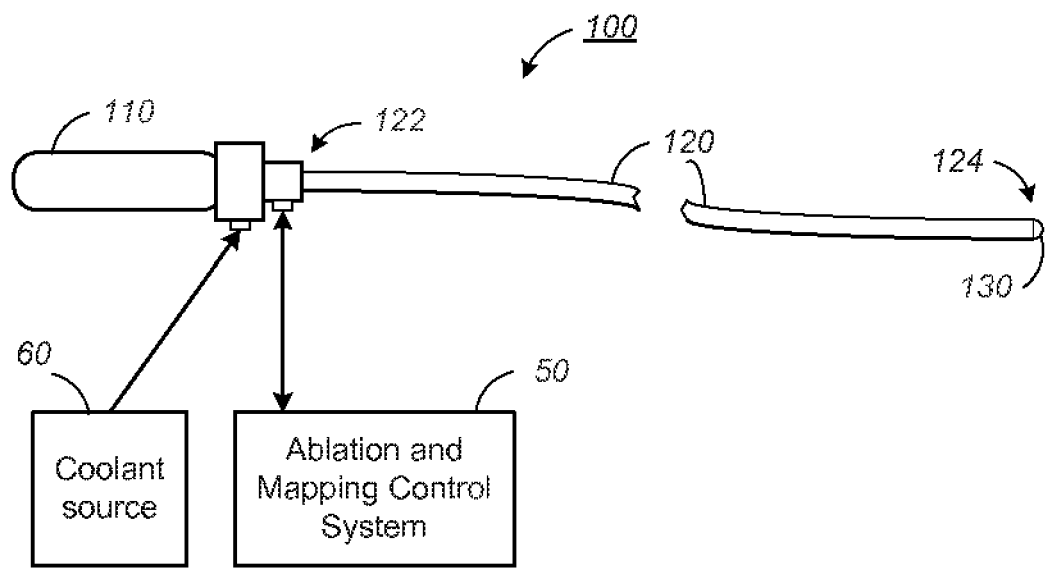
FIG. 5 illustrates a catheter with an irrigated electrode, according to a preferred embodiment of the invention.

FIG. 5 illustrates a catheter with an irrigated electrode, according to a preferred embodiment of the invention. The catheter 100 has an elongated housing 120 with a proximal end 122 and a distal end 124. An electrode 130 forms a tip electrode at the distal end. At the proximal end, the catheter terminates with a handle 110. At the proximal end, electrical connections are allowed to interface with an external ablation and mapping control system 50. Also a fluid port allows coolant from a coolant source 60 to be supplied into the catheter.

Figure 6:
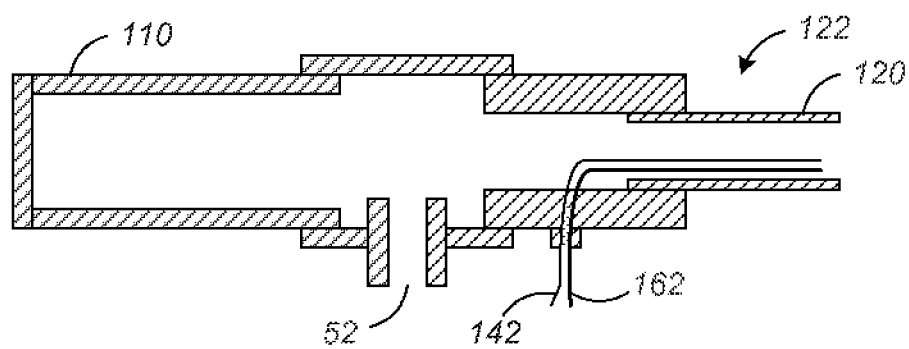
FIG. 6 illustrates a cross-sectional view of the catheter near the proximal end.

FIG. 6 illustrates a cross-sectional view of the catheter near the proximal end. The elongated housing 120 has an internal chamber that allows electrical conductors such as wires 152 and 162 to be run from the distal end and to be outlet at the proximal end 122. A fluid port 52 at the proximal end 122 near the handle 110 allows coolant to be supplied into the internal chamber of the elongated housing 120.

Figure 7:
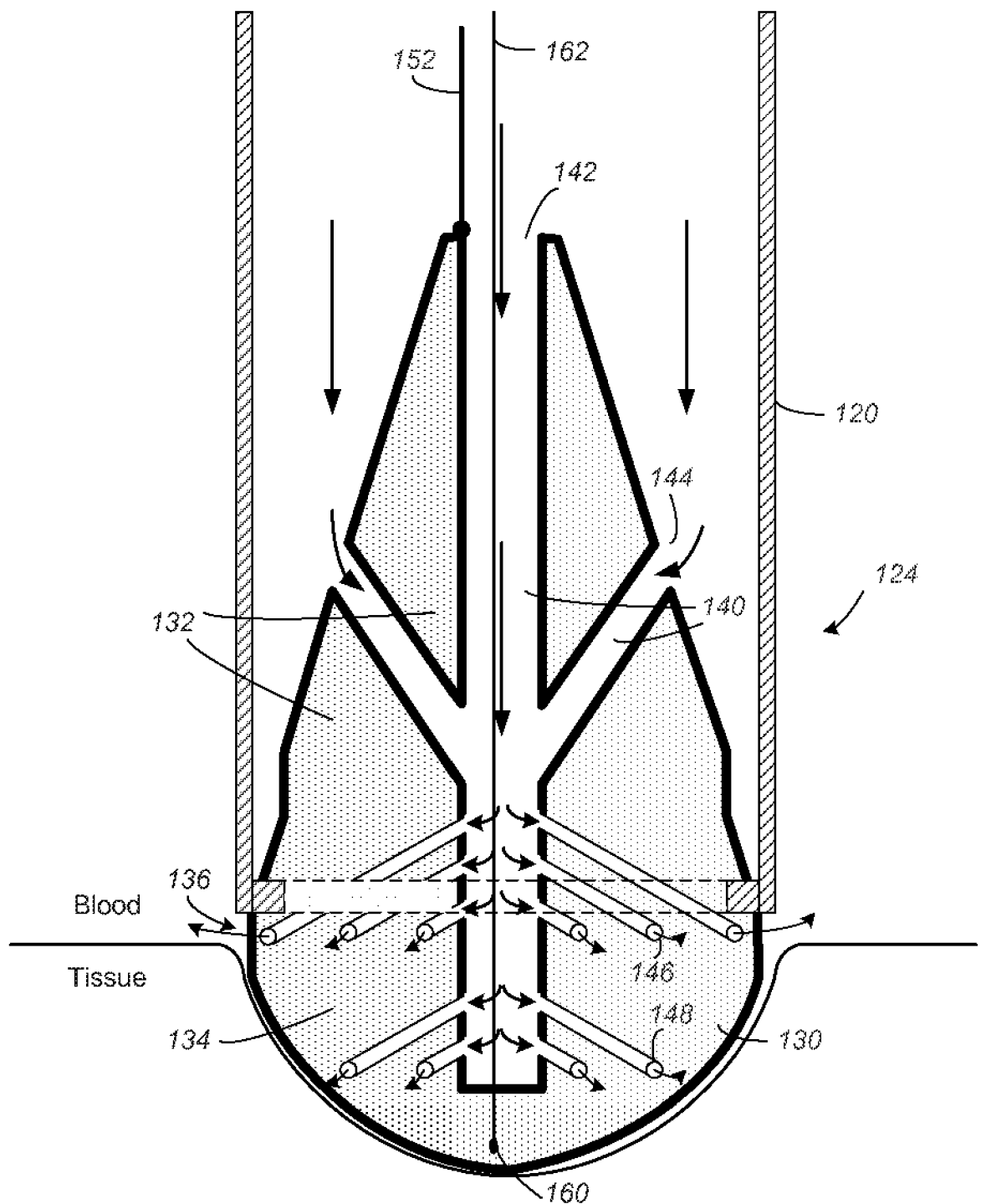
FIG. 7 illustrates a cross-sectional view of the electrode at the distal end of the catheter, according to a preferred embodiment of the invention.

FIG. 7 illustrates a cross-sectional view of the electrode at the distal end of the catheter, according to a preferred embodiment of the invention. The electrode 130 is an electrically conductive body located at the tip of the distal end 124 of the catheter. The wire 152 is connected to the electrode 130, and the wire 162 is connected to a temperature sensor 160 embedded in the electrode 130. In the preferred embodiment it has a pear-shape body, with a dome portion on one end and a cone portion on the opposite end. The electrode 130 is mounted at the distal end of the elongated housing 120 end such that the cone portion is enclosed inside the elongated housing and the dome portion is exposed outside of the catheter. In this way, the electrode 130 is partitioned into two portions, a first portion 132 inside the catheter and a second portion 134 outside the catheter.

During ablation, the catheter is disposed, for example, inside a heart chamber filled with blood. The second portion 134 of the electrode that is on the exterior has a surface and a shape that when disposed to ablate a tissue in the endocardium will have its surface in contact with the tissue surface 80 and be substantially covered by the tissue. In most cases, almost the entire second portion is covered by the tissue. At most, a minimum uncovered area 136 of the second portion (less than 35% of the surface area of the second portion) is not covered by the tissue and be exposed to blood. A preferred shape of the second portion 134 is a dome with a diameter of 2.3 mm and a height of 1.5 to 2 mm.

The first portion 132 of the electrode that is enclosed inside the catheter preferably has an elongated cone shape that provides a substantially larger surface area than that of the second portion 134 in order to provide an adequate area for heat exchange with the coolant. Other shapes for the first portion are also possible as long as sufficient surface area is available for heat exchange.

The electrode 130 is preferably a solid body with good thermal conductivity. This together with its extended body shape provide an electrode with much better heat capacity than that of a conventional hollow shell electrode, resulting in better temperature control at the electrode-tissue interface.

The electrode 130 has channels 140 within its body. The channels 140 have inlets at the surface of the first portion 132 and outlets at the surface of the second portion 134. Coolant supplied into the elongated housing through the proximal end is channeled into the electrode body 130 via the inlets such as inlets 142, 144 and is expelled out of the outlets such as outlets 146, 148 on the surface of the second portion 134. In practice, the coolant is allowed to flow just prior to disposing the electrode against a tissue to be ablated. In this way, the coolant being expelled from the outlets 148 will help to clear the blood from the electrode-tissue interface as well as providing a conducting medium at the electrode-tissue interface. In particular the outlets 146 are situated in the area 136 on the second portion 134 near the boundary with the first portion 132. As described earlier, during ablation, the area 136 of the second portion of the electrode may possibly be not covered by the tissue and be exposed to blood. With the outlets 146 situated in the area 136, the expelling coolant helps to keep the blood away from the uncovered area 136 and prevent the blood from congregating near any hot spots. This will further minimize the formation of blood clot.

Figure 8:
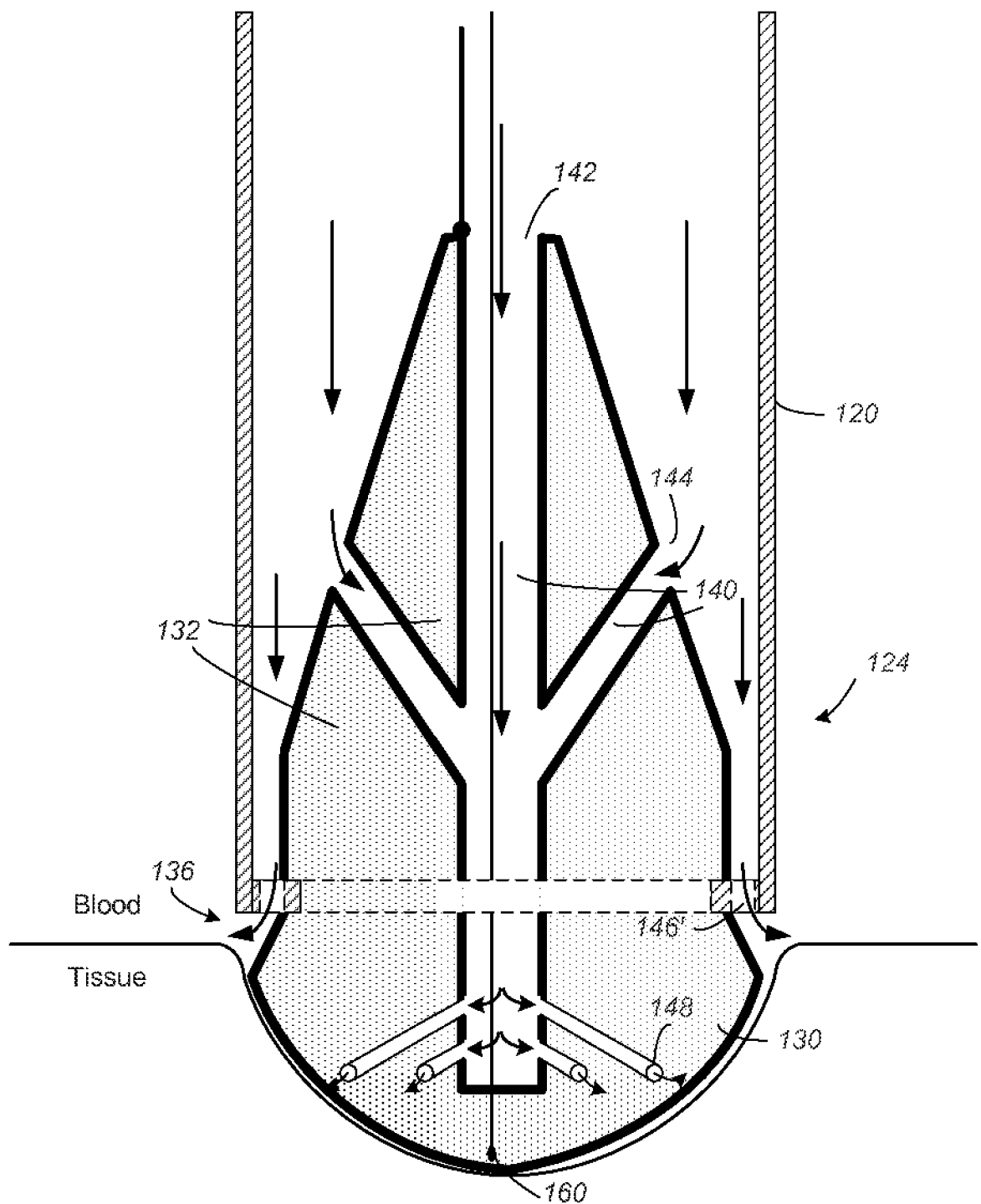
FIG. 8 illustrates another irrigated catheter, according to another preferred embodiment of the invention.

FIG. 8 illustrates another irrigated catheter, according to another preferred embodiment of the invention. The construction is similar to that shown in FIG. 7 except the outlets 146 near the area 136 is replaced by an annular opening 146' at the boundary between the first portion 132 and the second portion 134 of the electrode. Thus, the coolant is channeled into the electrode body 130 via the inlets such as inlets 142, 144 and is expelled out of the outlets such as outlets 146' and 148.

FIG. 9 is a table comparing the ablation operating characteristics of a conventional irrigated catheter with that of the improved catheter of the preferred embodiment. The results for the standard electrode are compiled from published data as well as from experiments performed on biological tissues in a laboratory. The results for the improved electrode are also obtained from experiments performed on biological tissues in the laboratory.

As can seen be from FIG. 9(A), the electrode size for the "Standard Electrode" is typical double the length of that of the "Improved Irrigated Electrode". The additional length allows more surface area cooling by blood. FIG. 9(B) shows for typical practice, at most 25% of the standard electrode is in contact with the tissue to be ablated, which leaves 75% of the electrode's surface exposed to blood for cooling. On the other hand, the improved catheter typically has a substantial portion of its exposed electrode surface in contact with the tissue and a relatively small portion is not covered by the tissue. FIG. 9(C) shows that the standard electrode is cooled by blood at 37° C. and possibly augmented by irrigated cooling with saline at 20.degree. C. On the other hand, the improved electrode only uses saline to cool an extended surface of the electrode. The extended surface of the electrode is shown in FIG. 7 as the first portion 132 of the electrode 130 and is not exposed to blood.

FIG. 9(D) shows that both electrodes are controlled to operate under the same temperature range which is optimized for lesion production without too much adverse effect. FIG. 9(E) shows that the operating conditions are set for each catheter to produce lesions of similar size. In that regard, it will be seen from FIG. 9(F) that the improved electrode requires about half the power (typically 15 W) to produce lesion of the same size. Furthermore, from FIG. 9(G) the lesion is formed in half the time compared to that by the standard electrode. Also, the cooling for the improved electrode is very efficient, requiring an order of magnitude lower in the volume of saline needed and yet achieving better cooling than that of the standard electrode. This is evidenced by field reports that overheating with steam pops do occasionally occur when ablating with such a standard electrode under similar conditions. As summarized in FIG. 9(I), owing to the efficient power usage and the superior cooling, the risk of steam pop is very low in the case of the improved electrode. Finally, FIG. 9(J) summarizes another advantageous feature of the improved electrode in that the risk of blood clot formation is much reduced compared to the conventional case since the portion of the electrode not covered by the tissue is at a minimum and blood is kept away from the uncovered portion by the effluent coolant there. With the blood kept at a distance from the uncovered part of the electrode, the cross-sectional area for the blood circuit is expanded, resulting in lower concentration of power dissipation and heating.

As shown in FIG. 9, the ablation electrode described in FIG. 7 and FIG. 8 will have the benefit of producing a reasonable size lesion efficiently and quickly and with minimum risk of blood formation. In operation, the distal end of the catheter is preferably incident on the tissue in a perpendicular direction to ensure maximum coverage of the electrode by the tissue.

According to yet another aspect of the invention, when an even larger lesion is desired or multiple lesions to be created in parallel in a procedure, the present inventive features are implemented in an improved multi-electrode catheter which spans a larger ablation zone. Each of the multiple electrodes will incorporate the inventive features. A suitable multi-electrode catheter for incorporating the present inventive features is similar to that disclosed in U.S. Pat. No. 6,738,673, the entire disclosure of which is incorporated herein by reference.

Figure 10A:
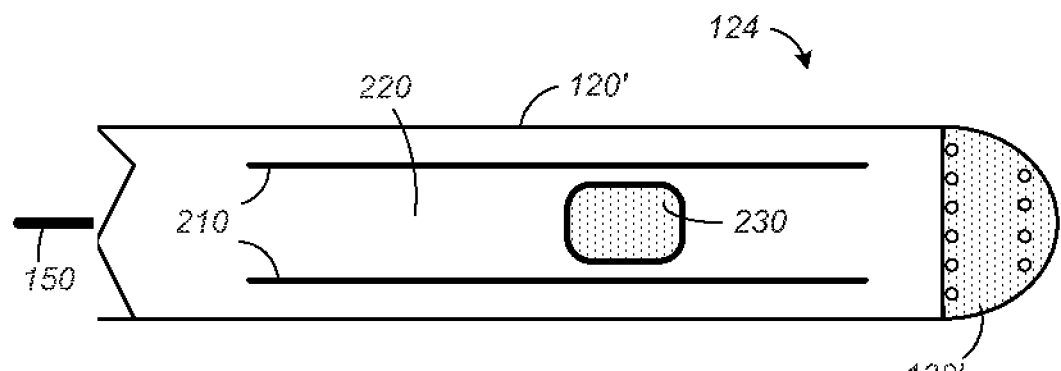
FIG. 10A illustrates the distal end of an irrigated multi-electrode catheter, according to another preferred embodiment of the invention.

FIG. 10A illustrates the distal end of an irrigated multi-electrode catheter, according to another preferred embodiment of the invention. Essentially, the distal end of the elongated housing 120' has, in addition to the electrode 130', a plurality of peripheral electrodes 230. An example is four peripheral electrodes 230 equally space around a circumfluence of the elongated housing 120' at a predetermined distance from the tip electrode 130'. In this way, the catheter comprises a plurality of electrodes 230 and a centrally located electrode 130'. The electrodes are capable of being collapsed onto the catheter body when the catheter is being introduced into a patient's body.

Figure 10B:
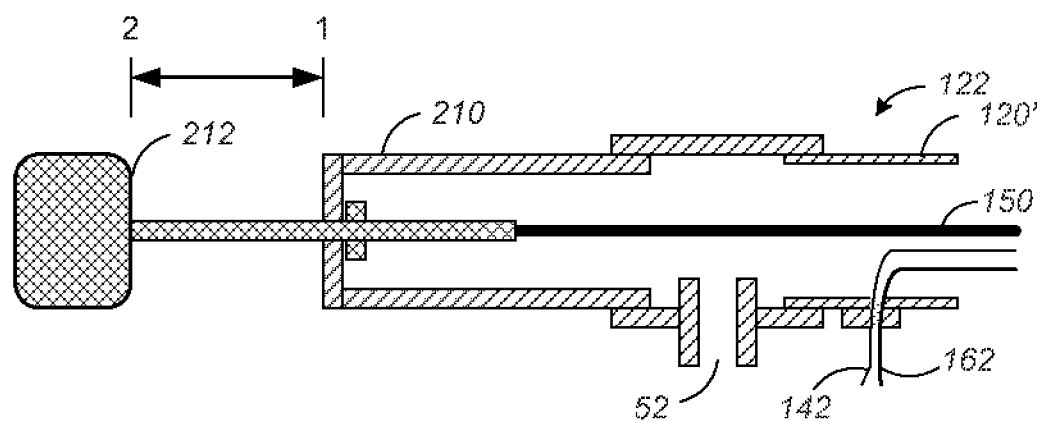
FIG. 10B illustrates the proximal end of the irrigated multi-electrode catheter shown in FIG. 10A.

FIG. 10B illustrates the proximal end of the irrigated multi-electrode catheter shown in FIG. 10A. The construction is similar to that shown in FIG. 6 except it further includes an actuator 212 at the handle 210. The actuator 212 is mechanically linked to the tip electrode 130' by a stiff cable 150.

Figure 10C:
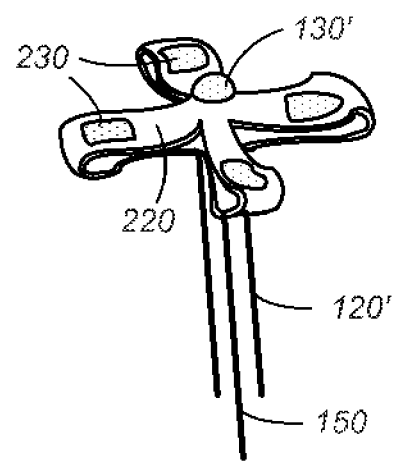
FIG. 10C illustrates that during ablation operation, the peripheral electrodes shown in FIG. 10A are deployed as fanned out into a two-dimensional or three-dimensional array.

FIG. 10C illustrates that during ablation operation, the peripheral electrodes shown in FIG. 10A are deployed as fanned out into a two-dimensional or three-dimensional array. The four peripheral electrodes are actuable from a retracted or collapsed mode. When fanned out, the four peripheral electrodes and the central electrode form an electrode array that typically covers an area of about 0.8 cm$^2$. When used with a conventional RF power source in conjunction with a backplate, the five connecting electrodes will typically produce five lesion spots simultaneously distributed over the area spanned by the electrode array.

A preferred implementation has the elongated housing formed from a deformable material. The peripheral electrodes 230 themselves may be made conveniently of a highly conductive material, such as gold or platinum. They have a shape and profile that provide maximum contact with and coverage by the tissue to be ablated. A plurality of longitudinally directed slits 210 are cut through the elongated housing 120 from a point adjacent to the tip electrode 130' to a predetermined distance away from the distal end. For example, for a distance of 1 cm between the peripheral electrode and the central electrode, the predetermined distance will be approximately 2 to 2.5 centimeters. Other inter-electrode distances between a peripheral electrode and the central electrode in the deployed mode are also contemplated. Also, other numbers of peripheral electrodes are contemplated. The slits define and form intermediate limbs 220 therebetween. The outer diameter of the elongated housing 120' itself may conveniently be about 2.34 millimeters. Referring also to FIG. 10B, when the actuator 212 is in a first position (1), the cable 150 together with the tip electrode 130' are fully extended towards the distal end resulting in the peripheral electrodes being collapsed onto the undeformed surface of the elongated housing 120' as shown in FIG. 10A. When the actuator 212 is in a second position (2), the cable 150 is retracted together with the tip electrode 130' by a predetermined amount towards the proximal end resulting in deforming the elongated housing at the slits 210. The limbs 220 open up and raise the peripheral electrode 230 away from the axis of the elongated body 120' in such a way that the peripheral electrode 230 lie in the same plane as the tip electrode 130 at their center.

Figure 11:
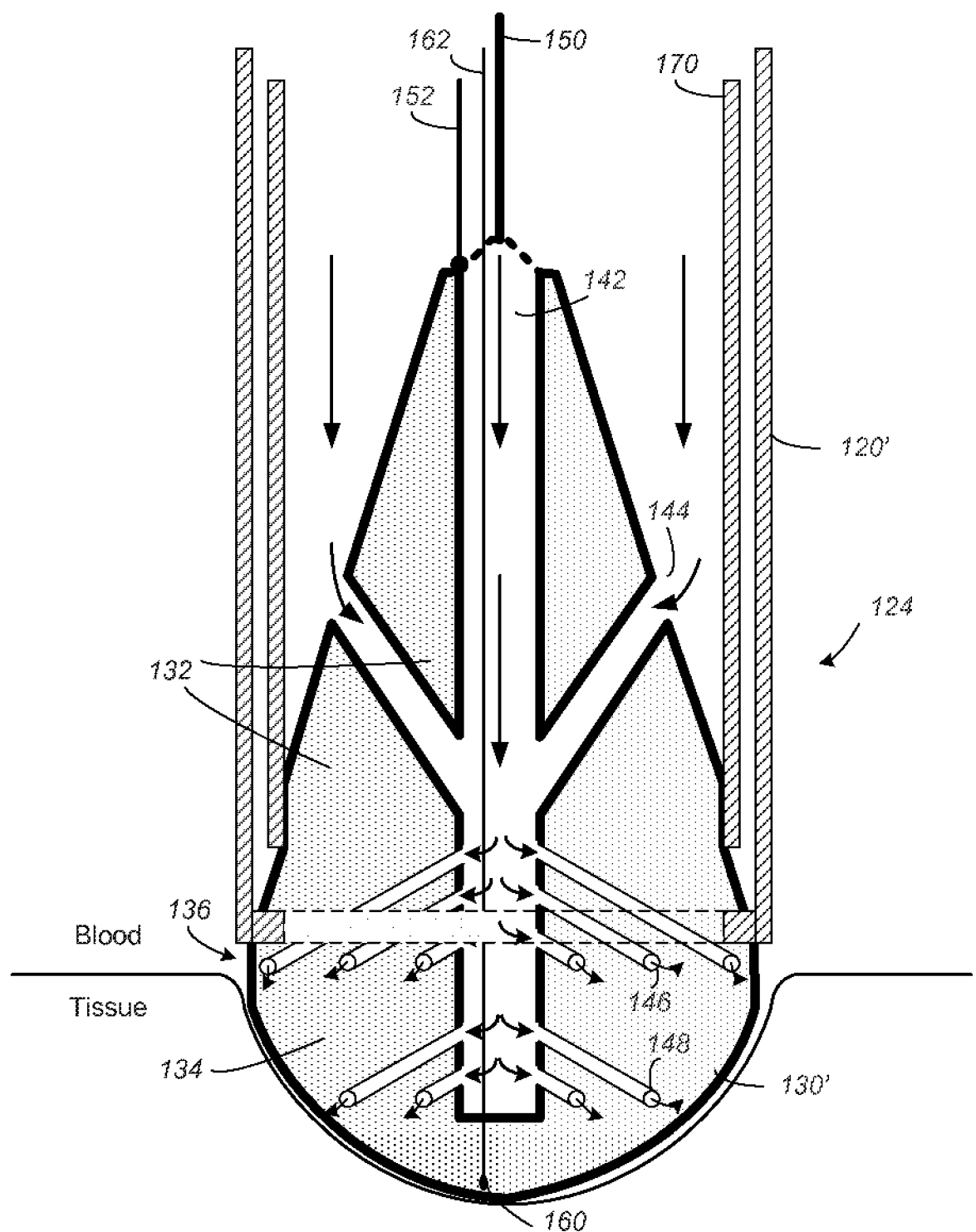
FIG. 11 illustrates a preferred embodiment of the tip electrode of the irrigated multi-electrode catheter shown in FIGS. 10A-10C.

FIG. 11 illustrates a preferred embodiment of the tip electrode of the irrigated multi-electrode catheter shown in FIGS. 10A-10C. The tip electrode 130' is essentially similar to that shown in FIG. 7 except that it additional has the cable 150 linking the tip electrode 130' and the actuator 212. Also, since the elongated housing 120' is no longer fluid tight with the slits 210, a fluid tube 170 provides a fluid tight circuit with the coolant port 52 (see FIG. 10B) and prevent leakage through the slits. The fluid tube has latitude that it remains in tight fluid connection irrespective of the position of the actuator 212 or the tip electrodes 130'.

In an example of operation, the actuator 212 at the proximal end is at position 1 and the catheter 100 with the collapsed peripheral electrodes is percutaneously introduced into a patient and directed through a blood vessel (not shown) and into the aorta 19, as best seen in FIG. 1. The distal end 124 is then positioned against an endocardial wall. The actuator 212 is then moved to position 2. This causes the tip electrode 130' to be withdrawn from their first position towards the proximal end while the peripheral electrodes 230 are deployed as best shown in FIG. 10C. In this position, the plurality of peripheral electrodes 230, are positioned equidistant from the electrode 130' at their center and at a second distance which is greater than the first distance. The distance between adjacent peripheral electrodes is conveniently about one centimeter. In this manner, an area of about one square centimeter of the endocardial wall is covered with the electrode 130' at the center of the square centimeter. As may be seen, the peripheral electrodes 230 are located on the upper half of the limbs formed by slits 210 so that the electrodes are presented facing the distal direction. Each peripheral electrode is connected to a respective one of the electrically conductive wires, which are routed out of the catheter at the proximal end.

FIG. 12A and FIG. 12B respectively illustrates the detail of coolant fluid connection when the peripheral electrodes are not deployed and when they are deployed, according to yet another preferred embodiment of the invention. In this preferred embodiment, the fluid tube 170 provides a fluid tight circuit with the coolant port 52.

FIG. 12A illustrates the relation between the coolant fluid tube and the tip electrode when the peripheral electrodes are not in a deployed configuration. At the distal end, the fluid tube is offset and disengaged from the first portion 132 of the tip electrode when the peripheral electrodes 230 are not in a deployed configuration.

FIG. 12B illustrates the relation between the coolant fluid tube and the tip electrode when the peripheral electrodes are in a deployed configuration as shown in FIG. 10C. At the distal end, the tip electrode 130' is withdrawn towards the open fluid tube so that the first portion 132 of the tip electrode 130' is totally enclosed in sealed relation with a receptacle 172 provided by the opening of the fluid tube. In this way, when in the deployed position, the fluid is allowed to cool the second portion 132 of the tip electrode 130' without leakage and without exposing the second portion 132 to any blood in the vicinity.

Figure 13A:
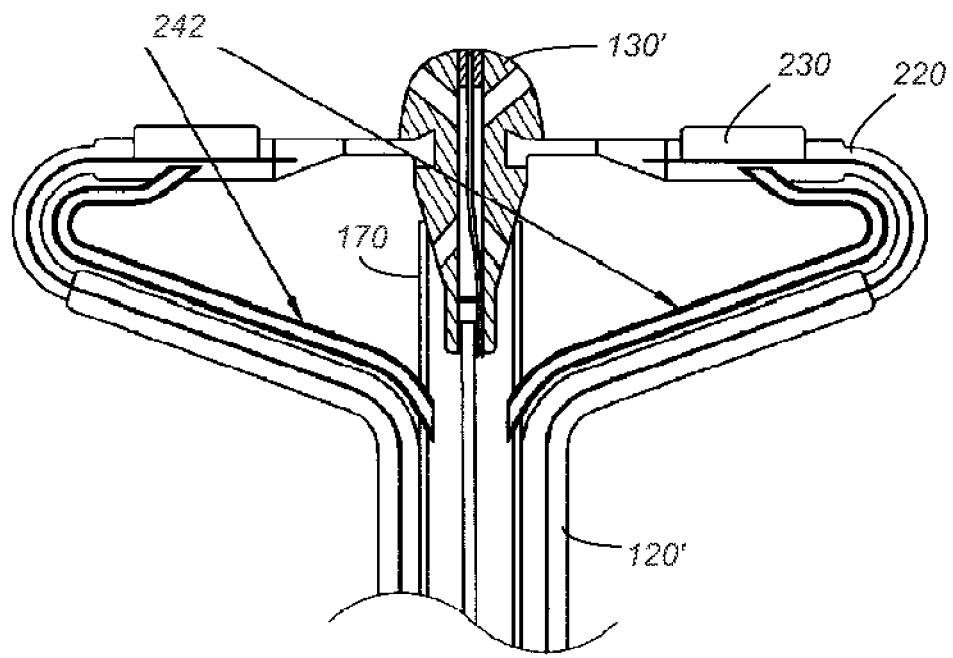
FIG. 13A illustrates the details irrigation of the peripheral electrodes of the multi-electrode catheter.

FIG. 13A illustrates the details of the irrigation of the peripheral electrodes of the multi-electrode catheter. Irrigation channel 242 is provided for each peripheral electrode 230, acting as a tributary channel to feed coolant from the fluid tube 170 to each peripheral electrode 230. Each irrigation channel 242 runs along an individual intermediate limb 220 to reach a chamber 244 enclosing the peripheral electrode 230.

Figure 13B:
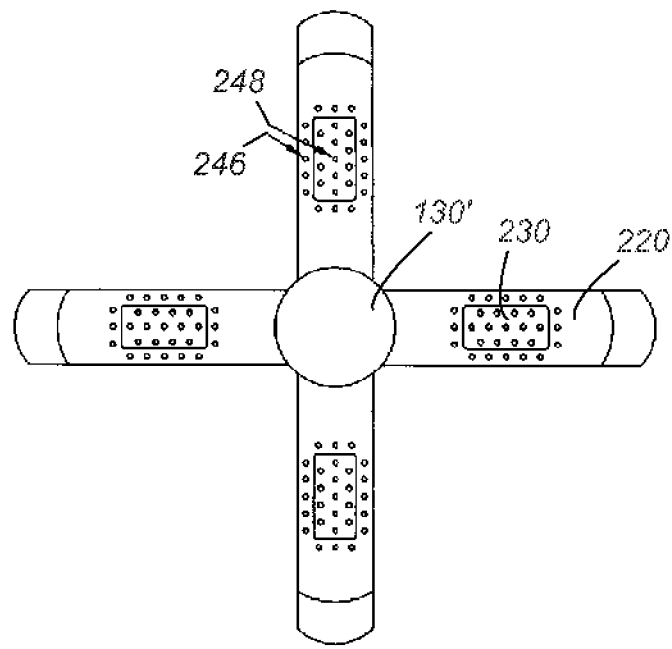
FIG. 13B illustrates a plan view of the deployed peripheral electrodes from the proximal direction.

FIG. 13B illustrates a plan view of the deployed peripheral electrodes from the distal direction. Irrigation outlets 246 are provide on the intermediate limb 220 adjacent the peripheral electrode 230. Outlets 248 are also provided on the electrode 230 to allow the coolant to exit from the chamber 244 to outside of the electrode.

According to another aspect of the invention, the improved electrode is preferably incorporated in a catheter that can have wings fanned out to form a plane with the electrode at the center. In this way, when the catheter is disposed against a tissue, the plane will be hugging the tissue surface and the electrode will impinge on the tissue in a perpendicular direction. The intermediate limbs 220 described in FIGS. 10A and 10C will serve as the wings.

The improved multi-electrode catheter described in FIGS. 10-13 greatly improves the performance and safety of procedures that involve multiple ablation operations.

One of the most prevalent cardiac arrhythmia is Atrial Fibrillation. This is the most sustained symptomatic arrhythmia with 2.5 million patients in USA and more than 5 million patients world wide. Based on recent population study the number will quadruple in next few decades. The seriousness of this problem is placed into perspective by its well described clinical sequel like thromboembolism resulting in stroke, congestive heart failure, cognitive dysfunction and possibly increased mortality. The magnitude of this problem is appreciated by the burden of great demand for treatment of Atrial fibrillation in the general population, placing stress on the health care system. Among older population over age 65, 5.8% have Atrial fibrillation, which amounts to 11% of the hospitalized population; 30% of patients with coronary artery disease and 30-40% with heart failure have this arrhythmia. According to Framingham Study one in every four person will develop this arrhythmia in his or her lifetime.

In a majority of these patients standard antiarrhythmic medication are ineffective to restore Normal Sinus Rhythm. Over the last ten years Radio-frequency catheter ablation of this arrhythmia has been evolving and has made significant progress. The source of this arrhythmia is presumed to be in and around four pulmonary veins in the left atrium. The catheter ablation of these arrhythmia is performed by various techniques including purely anatomical Pulmonary Vein Antrum Isolation ("PVAI"), Electrical Isolation of Common Triggers, Substrate Modification and combination of these various techniques.

As most commonly practiced, the procedure is performed by inserting a circular mapping catheter and a standard 3.5 mm irrigation ablation catheter in the left atrium via a double transeptal approach. Additional catheters are placed to map and pace the coronary sinus, His bundle, right atrium and right ventricle. In the left atrium 40-60 irrigation radiofrequency ablations are performed around the four pulmonary veins and in the posterior wall of the left atrium. During each ablation 35 to 50 watts of power is delivered at 40 to 50 degree Celsius through a temperature controlled Radiofrequency Generator. The saline irrigation fluid used during each ablation is 30 ml/min. The total procedure time is greater than 3 hours and the total fluid used during the entire procedure including the period during mapping and positioning the electrode is greater than 3000 ml or 3 Liters. As described above, this population of vulnerable patients is prone to heart failure because of significant fluid overload (3 liters of saline infused into a total blood volume of 5 Liters).

The high power of 40-50 watts used by standard irrigation catheter and its large exposure to blood has the potential for creating complications like: thromboembolism, esophageal injury, pericardial effusion and cardiac tamponade. Left atrium is a thin walled structure 3-4 mm thick. Esophagus is located just behind the posterior wall of the left atrium and is about 3-4 mm from the Epicardial wall of the left atrium. Esophageal injury is a devastating complication and currently occurs in 1% of patients undergoing these standard ablation procedures. One recent study demonstrated asymptomatic esophageal ulceration in 6 to 36% patients.

Current practice of Radiofrequency catheter ablation of atrial fibrillation has a success rate of 65 to 85% in various studies. The current technique is highly technical and demanding and can only be performed by few skilled and experienced Electrophysiologist in specialized centers with large referral base. The waiting lists in these centers are on average 18-24 months. This long delay is directly related to the difficulties associated with current standard radiofrequency ablation catheter technology, such as greater than 3 hours procedure time, and many complexities that can result in serious complications.

The present improved ablation catheter greatly improves the performance and safety of this procedure. The improved catheter will reduce the procedure time to less than 1 hour, reduce the fluid infusion into the patient during the procedure from 3000 ml to 200 ml, reduce the power from 40-50 watts/ablation to less than 15 watts/ablation and minimize all serious complications and make radiofrequency ablation of atrial fibrillation simple and universally available for all Electrophysiologist.

FIG. 14 is a table comparing projected ablation operating characteristics of different catheters in an ablation procedure to treat atrial fibrillation. The catheters being compared are: 1) Catheter with a standard electrode; 2) Catheter with the improved electrode, such as that shown in FIG. 7 and FIG. 8; and 3) Catheter with improved multiple electrodes, such as that shown in FIGS. 10-13. The comparisons are projected for requirements and conditions under an actual procedure with ablations over multiple sites such as one to treat atrial fibrillation. A comparison between the standard electrode and the improved electrode has been given earlier in FIG. 9 for one instance of ablation at a site.

FIGS. 14(A) and 14(B) respectively illustrates the RF power and application time required for the three catheters in order to produce a lesion of similar size. FIG. 14(C) shows that for treating atrial fibrillation, typically 40-60 sites will need to be ablated for a single electrode. In the case of the 5-electrode catheter, the number of sites will correspond to 8-12 sites.

Before each ablation, the catheter must be maneuvered to the site to be ablated. The maneuvering is often guided by mapping. In standard practices, the mapping is performed by another mapping catheter. Once the mapping catheter has identified the site, the ablation catheter will then be positioned at the site. FIG. 14(D) lists the total times for ablation and for mapping. Using the data listed in FIG. 9, the ablation time for 60 sites will be about one hour and the time for repositioning guided by mapping will be another hour. The catheter with the improved electrode will be similar except the ablation time is halved, which amounts to 1.5 hours. The catheter with the multiple electrodes will be shorter still since 5 sites are ablation in parallel and the total number of repositioning is accordingly reduced.

FIG. 14(E) compares the amount of coolant ejected into the patient's blood system during the procedure. It is well known that performing such a procedure with a standard catheter will result in dumping 3000 ml of coolant into the patient's blood system. In comparison, the improved catheter, be it single or multiple only release one order of magnitude less coolant.

FIG. 14(F) shows that mapping is also needed to monitor the quality of the lesion. A good lesion is indicated by a much attenuated intracardiac electrogram.

FIG. 14(G) is similar to FIG. 9(I). Owing to the efficient power usage and the superior cooling, the risk of steam pop is very low in the case of the improved electrode.

Finally, FIG. 14(H) is similar to FIG. 9(J). Another advantageous feature of the improved electrode in that the risk of blood clot formation is much reduced compared to the conventional case since the portion of the electrode not covered by the tissue is at a minimum and blood is kept away from the uncovered portion by the effluent coolant there.

While the embodiments of the various aspects of the present invention that have been described are the preferred implementation, those skilled in the art will understand that variation thereof may also be possible. The device and method described therein are applicable to ablation of biological tissues in general. Therefore, the invention is entitled to protection within the full scope of the appended claims.

What is claimed:

1. A method of ablating cardiovascular tissue, comprising:
positioning an electrode mounted on a distal end of a catheter in contact with cardiovascular tissue to be ablated, the distal end of the catheter terminating directly adjacent to and being immovable relative to a widest width of the electrode such that at least 65 percent of an exposed distal surface area of the electrode is in contact with the cardiovascular tissue to be ablated, a proximal surface area of the electrode within the catheter being larger than the exposed distal surface area;
irrigating the electrode with an irrigation fluid delivered through the catheter; and
applying radiofrequency (RF) energy to the electrode in order to ablate the cardiovascular tissue.

2. The method of claim 1, wherein the electrode is positioned such that any exposed distal surface area of the electrode not in contact with the cardiovascular tissue is in contact with blood.

3. The method of claim 1, wherein irrigation of the electrode includes delivering the irrigation fluid through a plurality of channels located within the electrode.

4. The method of claim 1, wherein irrigation of the electrode includes using the irrigation fluid to flush the exposed distal surface area of the electrode not in contact with the cardiovascular tissue.

5. The method of claim 1, further comprising monitoring a temperature of the electrode.

6. The method of claim 1, further comprising expanding a plurality of secondary electrodes radially around the electrode on the distal end of the catheter.

7. The method of claim 1, wherein applying of RF energy includes forming a discrete lesion in the cardiovascular tissue having a surface area that is greater than the exposed distal surface area of the electrode that is in contact with the cardiovascular tissue.

8. The method of claim 7, wherein a diameter of the lesion is 6 millimeters or greater.

9. The method of claim 1, wherein the RF energy applied is between about 4 watts and about 15 watts.

10. The method of claim 1, wherein the RF energy is delivered to the cardiovascular tissue for a duration of about 30 seconds or less.

11. The method of claim 1, wherein the irrigation fluid is delivered at an irrigation rate that is less than about 30 milliliters per minute.

12. The method of claim 1, wherein the irrigation fluid is delivered at an irrigation rate of about 1 to about 2 milliliters per minute.

13. The method of claim 1, wherein ablation of the cardiovascular tissue is for treating atrial fibrillation.

14. The method of claim 13, wherein a total amount of the irrigation fluid delivered during a procedure to treat atrial fibrillation is about 200 milliliters or less.

15. The method of claim 1, wherein at least 50 percent of a total RF energy that passes out of the catheter through the electrode during ablation of the cardiovascular tissue passes through the tissue to be ablated.

16. The method of claim 1, wherein the exposed distal surface area of the electrode includes at least all of an outer surface of the electrode distal to the widest width of the electrode.

17. The method of claim 1, wherein the electrode has a pear-shape body with a dome portion on a distal end and a cone portion on an opposite proximal end, and the exposed distal surface area includes at least the dome portion.

18. The method of claim 17, wherein the exposed distal surface area includes only the dome portion, and the cone portion is entirely enclosed by the distal end of the catheter.

19. The method of claim 1, wherein the electrode has a pear-shape body with a dome portion on a distal end and a cone portion on an opposite proximal end, and the exposed distal surface area includes at least the dome portion.

20. A method of ablating cardiovascular tissue, comprising:

positioning an electrode mounted on a distal end of a catheter in contact with cardiovascular tissue to be ablated, the distal end of the catheter terminating at and being immovable relative to a widest width of the electrode such that at least 65 percent of an exposed distal surface area of the electrode is in contact with the cardiovascular tissue to be ablated, a proximal surface area of the electrode within the catheter being larger than the exposed distal surface area;

irrigating the electrode with an irrigation fluid delivered through the catheter at an irrigation rate that is less than about 30 milliliters per minute; and applying between about 4 watts and about 15 watts of radiofrequency (RF) energy to the electrode in order to ablate the cardiovascular tissue to form a discrete lesion in the cardiovascular tissue having a surface area that is greater than the exposed distal surface area of the electrode that is in contact with the cardiovascular tissue.

21. The method of claim 20, wherein the RF energy is delivered to the cardiovascular tissue for a duration of about 30 seconds or less.

22. The method of claim 20, wherein at least 50 percent of a total RF energy that passes out of the catheter through the electrode during ablation of the cardiovascular tissue passes through the tissue to be ablated.

23. The method of claim 20, wherein ablation of the cardiovascular tissue is for treating atrial fibrillation.

24. The method of claim 20, further comprising expanding a plurality of secondary electrodes radially around the electrode on the distal end of the catheter.

* * * * *